US009670466B2

(12) United States Patent
Tratschin et al.

(10) Patent No.: US 9,670,466 B2
(45) Date of Patent: *Jun. 6, 2017

(54) PESTIVIRUS REPLICONS PROVIDING AN RNA-BASED VIRAL VECTOR SYSTEM

(71) Applicant: INSTITUT FUR VIRUSKRANKHEITEN UND IMMUNPROPHYLAXE, Mittelheausern (CH)

(72) Inventors: Jon Duri Tratschin, Bolligen (CH); Nicolas Ruggli, Mittelhausern (CH); Kenneth Charles McCullough, Cousset (CH)

(73) Assignee: INSTITUT FUR VIRUSKRANKHEITEN UND IMMUNPROPHYLAXE, Mittelhausern (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/978,647

(22) Filed: Dec. 22, 2015

(65) Prior Publication Data

US 2016/0108372 A1 Apr. 21, 2016

Related U.S. Application Data

(63) Continuation of application No. 12/995,874, filed as application No. PCT/EP2009/003892 on May 30, 2009, now Pat. No. 9,249,395.

(30) Foreign Application Priority Data

Jun. 4, 2008 (EP) ..................... 08010222

(51) Int. Cl.
*C12N 7/00* (2006.01)
*A61K 9/00* (2006.01)
*A61K 39/00* (2006.01)

(52) U.S. Cl.
CPC ............... *C12N 7/00* (2013.01); *A61K 39/00* (2013.01); *A61K 2039/5256* (2013.01); *C07K 2319/00* (2013.01); *C12N 2770/24323* (2013.01); *C12N 2770/24342* (2013.01); *C12N 2770/24343* (2013.01); *C12N 2840/203* (2013.01)

(58) Field of Classification Search
None
See application file for complete search history.

(56) References Cited

U.S. PATENT DOCUMENTS

| 7,829,319 | B2 * | 11/2010 | Werther | C07K 1/22 |
| | | | | 435/219 |
| 9,249,395 | B2 * | 2/2016 | Tratschin | C12N 7/00 |

| 2003/0165520 | A1 | 9/2003 | Cao et al. | |
| 2005/0208071 | A1 * | 9/2005 | Beer | A61K 39/12 |
| | | | | 424/204.1 |
| 2005/0220813 | A1 | 10/2005 | Widjojoatmodjo et al. | |

FOREIGN PATENT DOCUMENTS

| WO | WO0053766 | 9/2000 |
| WO | 2004092386 | 10/2004 |
| WO | WO 2004092386 | * 10/2004 |
| WO | 2007066188 | 6/2007 |

OTHER PUBLICATIONS

Jon-Duri Tratschin et al., "Classifical Swine Fever Virus Leader Proteinase N pro is Not Required for Viral Replication in Cell Culture", Journal of Virology, vol. 72, No. 9, Sep. 1, 1998, pp. 7681-7684.
Caroline F. Frey et al., "Classical fever virus replicon particles lacking the Erns gene: a potential marker vaccine for intradermal application", Veterinary Research 2006, vol. 37, No. 5, pp. 655-670.
Christian Moser et al., "A Recombinant Classical Swine Fever Virus Stably Expresses a Marker Gene", Journal of Virology, Jun. 1998, vol. 72, No. 6, pp. 5318-5322.
Ruggli et al., "Nucleotide Sequence of Classical Swine Fever Virus Strain Alfort/187 and Transcription of Infectious RNA from Stably Cloned Full-Length cDNA", Journal of Virology, vol. 70, No. 6, Jun. 1996, p. 3478-3487.
Mayer et al. (Vaccine. 2004; 22: 317-328).
Agapov et al. (Hournal of Virology. 2004; 78 (5): (2414-2425).
Vassilev et al. (Vaccine. 2001; 19: 2012-2019).
Hilton et al. (Hournal of Virology. 2006; 80(23): 11723-11732).
Dow. Experimental Opinion Drug Delivery. Jan. 2008; 5 (1): 11-24).
Wilson et al. (Cell. 1979; 17: 77-84).
Tautz et al. (Journal of Virology. 1999; 73 (11): 9422-9432).
Elbers et al. (Journal of Virology. 1996I 70 (6): 4131-4135).

* cited by examiner

*Primary Examiner* — Shanon A Foley
(74) *Attorney, Agent, or Firm* — K&L Gates LLP

(57) ABSTRACT

Replicons of pestiviruses, in particular replicons of swine fever virus, are engineered to have a defective replication thereby having lost infectivity, and further containing a foreign gene. A replicon contains all the genetic information required for its replication, but lacks essential codons or all codons of at least one of the genes encoding the viral structural proteins E1, E2, E$^{ms}$ or C protein, and consequently cannot generate infectious virus particles. Particular replicons are generated with a mutated gene encoding a modified N$^{pro}$ protein that no longer controls the cell interferon-induction pathway. Another particular replicon lacks the genes encoding all the structural proteins, the p7 protein and the NS2 protein, and has cytopathogenic properties in transduced cells. The replicons provide a new vector system that can be used for vaccination, gene delivery and gene therapy applications in mammals, including humans, as naked RNA or packaged into any form of delivery vehicle.

19 Claims, 3 Drawing Sheets

A

B

PESTIVIRUS REPLICONS PROVIDING AN RNA-BASED VIRAL VECTOR SYSTEM

PRIORITY CLAIM

The present application is a continuation of U.S. patent application Ser. No. 12/995,874 filed on Dec. 2, 2010, which is a National Stage of International Application No. PCT/EP09/003892 filed on May 30, 2009, which claims priority to European Application No. 08010222.1 filed on Jun. 4, 2008, the entire contents of each of which are incorporated herein by reference.

FIELD OF THE INVENTION

The present invention concerns replicons of pestiviruses, in particular replicons of classical swine fever virus, engineered to lack the capacity to form infectious virus particles, and further containing a foreign gene. These replicons provide a new vector system that can be used for vaccination, gene delivery and gene therapy applications in mammalians, including humans, as naked RNA or packaged into appropriate particulate delivery vehicles, including replicons packaged into pestivirus particles.

BACKGROUND

Classical Swine Fever Virus (CSFV)

Classical swine fever virus (CSFV) is the causing agent of a highly contagious disease of pigs and wild boars, but is totally innocuous for humans. CSFV, together with bovine viral diarrhea virus and border disease virus of ovines, belongs to the genus *pestivirus* within the family *Flaviviridae*. The other members of the *Flaviviridae* are the genus *flavivirus* (prototype: yellow fever virus) and the genus *hepacivirus* (hepatitis C virus).

Pestiviruses are small enveloped viruses with a single-stranded 12.3 kb RNA genome of positive polarity containing one large open reading frame (ORF) flanked by 5' and 3' nontranslated regions. The ORF encodes a polyprotein that is composed of four structural and eight nonstructural (NS) proteins in the order $NH_2$—$N^{pro}$-C-$E^{rns}$-E1-E2-p7-NS2-NS3-NS4A-NS4B-NS5A-NS5B-$C_{OO}H$ (FIG. 1A). The structural components of the virion include the capsid protein C and the three envelope glycoproteins $E^{rns}$, E1, and E2. The leader autoprotease $NP^{pro}$ as well as $E^{rns}$—a glycoprotein with ribonuclease activity, which is both secreted and virus-associated—are unique to the genus pestivirus. $NP^{pro}$ is considered an accessory protein not required for virus replication, but having a role in the pathogenesis of the virus due to its capacity to interfere with the innate immune response. Furthermore, $N^{pro}$ is an autoprotease which cleaves itself off the nascent viral polyprotein thereby generating the amino-terminus of the capsid protein C. Proteins NS3 to NS5B are sufficient for replication of the viral RNA and are considered to form the RNA replication complex. Uncleaved NS2-NS3 as well as p7 are required for virus particle formation.

Manipulation of the genome of RNA viruses is only possible if corresponding cDNA clones, preferably inserted in plasmids, are available for stable propagation of the genetic information in bacterial cells. These clones are designed to allow in vitro transcription of authentic infectious viral RNA that can be transfected into susceptible cells where the viral RNA will replicate and eventually give rise to the generation of infectious virus. Over the past 15 years cDNA clones have been established for many viruses of the family *Flaviviridae*, including pestiviruses.

Following on the development of the pestivirus cDNA clones, a recombinant CSFV derived from strain Alfort/187 (Ruggli et al., J Virol 70, 3478-3487, 1996) with a stably inserted chloramphenicol acetyl transferase (CAT) gene was generated (Moser et al., J Virol 72, 5318-5322, 1998), demonstrating that a foreign gene can be expressed in fusion with the $NA^{pro}$ protein without affecting virus replication. Also, replacement of the entire $N^{pro}$ gene in CSFV by the murine ubiquitin gene did not impair the replication ability of the virus (Tratschin et al., J Virol 72, 7681-7684, 1998).

CSFV Replicons

By definition, a replicon represents a molecule that replicates autonomously in host cells. Therefore, the standard, full-length RNA genome of CSFV is the prototype CSFV replicon. Investigations using engineered cDNA of CSFV have been performed to determine the viral proteins required for RNA replication. This allowed the conclusion that the replication complex is composed of the 5 proteins NS3, NS4A, NS4B, NS5A, and NS5B. Subsequent to the above work, artificial replicons lacking the coding sequence for only one or several of the structural proteins, C, $E^{rns}$, E1, or E2, were generated (Frey et al., Vet Res 37, 655-70, 2006). Such replicons have to be complemented in cell lines constitutively expressing the respective, missing structural protein(s) of the virus, allowing the rescue of viral particles carrying the defective (replicon) genome. These defective CSFV particles are referred to as virus replicon particles (VRP).

CSFV Replicons as a Vaccine

CSFV replicons, in the form of the VRP, have been employed as experimental vaccines against CSFV in pigs, but not as vectors for human or other mammalian vaccination. VRP are infectious virions that contain subgenomic RNA with specific deletion(s) in at least one of the genes encoding the viral structural proteins. Such RNA replicates and expresses the encoded viral proteins in the host cell. However, due to the defect in at least one of the envelope proteins it cannot generate progeny VRP. VRP carrying a genome devoid of either the Ems or the E2 gene have recently been proposed as live-attenuated, non-transmissible CSF vaccines. Challenge with highly virulent CSFV of pigs parenterally vaccinated with VRP have shown that VRP lacking the $E^{rns}$ gene can be protective (Frey et al., Vet Res 37, 655-70, 2006). It was also noted that these VRP vaccines have the potential to induce both humoral and cell-mediated immunity.

Many vaccines in use today are based on inactivated virus, which tends to favor humoral immunity with little or no cell-mediated defense development. This may allow for the removal of free virus and some virus-infected cells through the action of antibodies, but antibodies cannot interact with virus in all compartments of the body. It is the cell-mediated immunity that can ensure removal of small foci of virus infected cells. Accordingly, if a vaccine could induce both humoral and cell-mediated immunity, the likelihood of a more solid immune defense would be forthcoming.

SUMMARY OF THE INVENTION

The present invention concerns replicons of pestiviruses, in particular replicons of classical swine fever virus (CSFV), engineered to lack the capacity to form infectious virus particles (FIGS. 1B to 1G), and further containing a foreign gene. The replicons retain the ability to replicate in mammalian cells, including human cells, when transfected into such cells.

In particular, the replicon lacks essential codons or all codons encoding one or more structural proteins required to form virus particles. The structural proteins of CSFV are the capsid protein C and the three envelope glycoproteins $E^{rns}$, E1, and E2. However, the replicon designed for expression of any foreign gene of interest retains all genetic information required for its replication in a mammalian cell including human cells. The foreign gene of interest may be a complete gene encoding a foreign protein or a nucleotide sequence encoding a portion of a foreign protein. The foreign gene may, for example, be inserted at the 5' end of the viral coding sequence, preferably within the $Ne^{pro}$ gene, or at the 3' end of the $N^{pro}$ gene in the context of a bicistronic genome (FIGS. 2B to 2E).

A particular form of the replicon further contains mutated codons in the $N^{pro}$ gene, for example a cysteine to arginine substitution at amino acid position 112 of $N^{pro}$ ($C_{112}R$) or an aspartic acid to asparagine substitution at position 136 ($D_{136}N$), such that the encoded mutant $N^{pro}$ protein has lost the ability to interfere with type 1 interferon (IFN) induction (referred to as $N^{pro}$ in FIGS. 1 and 2). In a further particular form of the replicon the $N^{pro}$ gene is deleted ($\Delta N^{pro}$ CSFV replicon), for the same purpose of creating a replicon that no longer encodes a protein capable of interfering with type I IFN induction.

Yet another particular form of the replicon lacks essential codons for the non-structural protein NS2, or the genes encoding NS2 and NS3 are physically separated by additional nucleotides, and consequently the replicon is cytopathogenic. In particular, all the sequences for C through NS2 may be lacking ($\Delta$C-NS2 CSFV replicon) (FIG. 1G). It is considered that the cytopathogenic phenotype may be advantageous with respect to the induction of cytotoxic immune defenses.

Replicons according to the invention provide a new vector system that can be used for vaccination, gene delivery and gene therapy applications in mammalians, including humans, either as naked RNA or associated with appropriate particulate delivery vehicles, for example replicons packaged into pestivirus particles.

The invention further concerns pharmaceutical compositions comprising a pestivirus replicon, alone or associated with appropriate particulate delivery vehicles, encoding foreign gene(s) having value for application as a vaccine. Accordingly, the invention relates to a method of prophylaxis against a disease caused by an infectious agent, by administering a replicon, alone or associated with appropriate particulate delivery vehicles, wherein the foreign gene incorporated into the replicon encodes a gene product immunizing against said infectious agent.

Furthermore, the invention concerns a method of treatment of a disease caused by a deficient gene, by administering a replicon, alone or associated with appropriate particulate delivery vehicles, wherein the foreign gene incorporated into the replicon is the functional gene associated with the disease.

Figure 1:
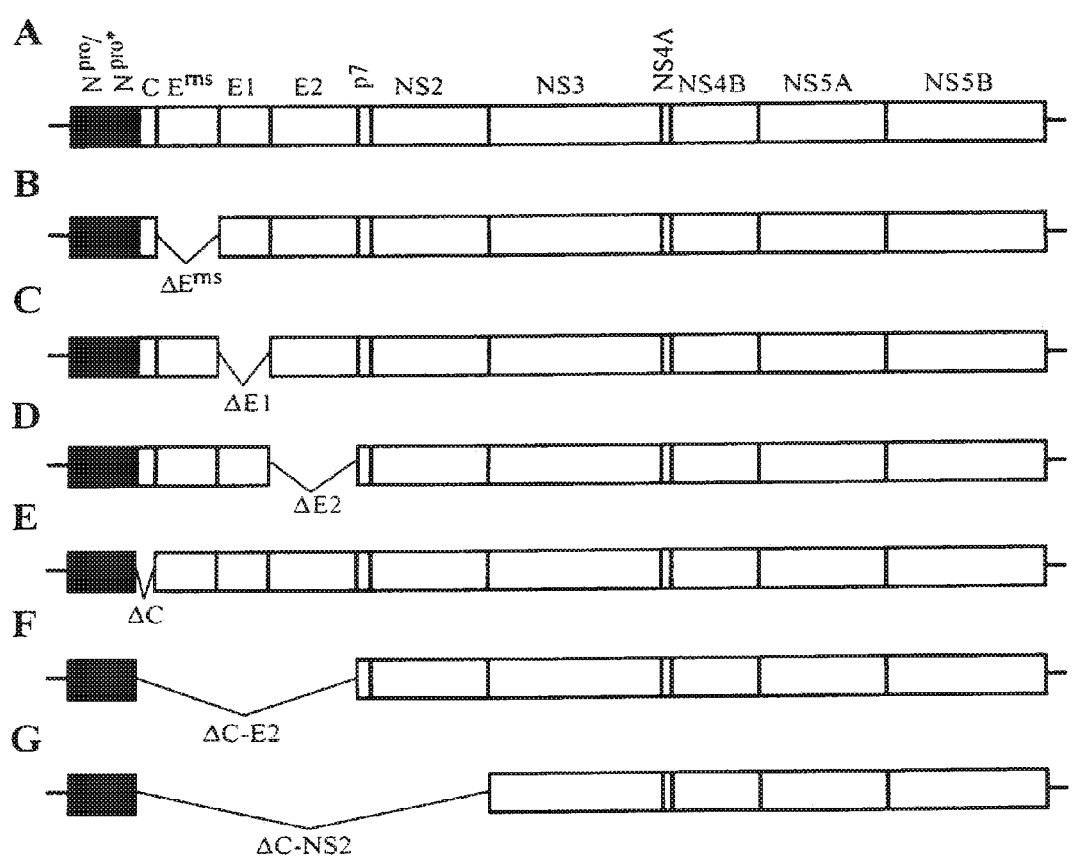
FIG. 1

Schematic display of standard, full-length and defective genomes (replicons) of CSFV vA187-1. The 5'- and 3'-UTRs (untranslated regions) are depicted as straight black lines, and the open reading frame is shown as a box composed of the individual viral genes encoding structural and nonstructural proteins (grey) as indicated, with the gene encoding the nonstructural $NP^{pro}$ protein shown as a black box. The nomenclature $N^{pro}$ refers to an $N^{pro}$ protein in which codons are mutated.

(A) Schematic representation of the gene sequence of the standard, full-length CSFV genome.

(B) to (G) Examples of CSFV replicon constructs in which selected genes are deleted without impairing the replication of the replicon: (B) CSFV replicon lacking the Ems gene ($\Delta E^{rns}$ replicon); (C) CSFV replicon lacking the E1 gene ($\Delta$E1 replicon); (D) CSFV replicon lacking the E2 gene ($\Delta$E2 replicon); (E) CSFV replicon lacking the C gene ($\Delta$C replicon); (F) CSFV replicon lacking the C, $E^{rns}$, E1 and E2 genes ($\Delta$C-E2 replicon); (G) CSFV replicon lacking the C, $E^{rns}$, E1, E2 and NS2 genes ($\Delta$C-NS2 replicon—the cytopathic or cp replicon).

FIG. 2

Schematic display of standard, full-length CSFV vA187-1 genome (A) and examples of defective genomes (replicons) derived from this construct (B to E), in which a heterologous gene ("Gene of Interest", GoI) has been inserted in monocistronic (B, D) and bicistronic (C, E) constructs. The shading and nomenclature is as in FIG. 1, with the GoI shown as a striped box. With the monocistronic construct, this is shown as being placed within the first 12 nucleotides at the 5' end of the $N^{pro}$ gene. With the bicistronic construct, the GoI is being placed immediately downstream of the $N^{pro}$ gene. The EMCV IRES required for the bicistronic construct is shown as a solid black line at the 3' end of the inserted GoI.

FIG. 3

The importance of the CSFV $N^{pro}$ protein for the modulation of IFN-$\alpha$/$\beta$ induction in both porcine and human cells. CSFV or the CSFV replicon modulation of IFN-$\alpha$/$\beta$ induction is dependent on the $N^{pro}$ protein, being absent when the $N^{pro}$ gene is deleted from the full-length viral genome or from the replicon (vA187-$\Delta N^{pro}$). The NPRo-dependent modulation of IFN-$\alpha$/$\beta$ induction can also be knocked out with either of two independent amino acid changes; $N^{pro}$ ($C_{112}R$) or $N^{pro}$ ($D_{136}N$) in the respective constructs.

(A) The porcine kidney cells, PK-15 cells, were mock-infected ("M") or infected at an MOI of 2 TCID50/cell with CSFV vA187-1, or with vA187-1-derived mutant viruses lacking the $N^{pro}$ gene (vA187-$\Delta N^{pro}$)), or carrying a cysteine to arginine substitution at amino acid position 112 of $NP^{pro}$ (vA187-$\Delta N^{pro}$ ($C_{112}R$)) or an aspartic acid to asparagine substitution at position 136 (vA187-$\Delta N^{pro}$ (0136N)), as indicated on the x-axis. Type I interferon (IFN-$\alpha$/$\beta$) bioactivity was measured as units per ml (y-axis) in cell culture supernatants using an Mx/CAT reporter gene assay and recombinant porcine IFN-a as standard for quantification. The detection limit is 2 U/ml.

(B) The human embryonic kidney cells, HEK293T cells, were transfected in duplicate wells with a mixture of three plasmids: the firefly luciferase reporter plasmid p125Luc (Ruggli et al., Virology 340, 265-276, 2005) for human IFN-$\beta$ promoter activity, plasmid phRL-SV40 (Promega) for constitutive expression of Renilla luciferase (for normalization), and a plasmid for expression of the $N^{pro}$ ($N^{pro}$) or mutated $N^{pro}$ ($N^{pro}$ ($C_{112}R$); $N^{pro}$ ($D_{136}N$)) protein as indicated on the x-axis. "C" refers to transfection with an expression plasmid encoding the capsid protein C, while "V" refers to transfection using the plasmid employed for expression of the $N^{pro}$, but lacking the $N^{pro}$ gene. After 24 h, one well was further transfected with 400 ng poly(IC) per 2×105 cells to induce IFN-$\beta$, and the second well was mock-transfected. After 18 h, the inducible firefly luciferase activity was normalized with the constitutively expressed *Renilla luciferase* activity, and the relative induction ("I") of poly(IC)-treated versus mock-treated cells was calculated. The results are the mean of three independent inductions with error bars representing the standard deviation.

DETAILED DESCRIPTION OF THE INVENTION

The present invention concerns replicons of pestiviruses, in particular replicons of classical swine fever virus, engineered to lack the capacity to form infectious virus particles, and further containing a foreign gene. The replicons retain the ability to replicate in mammalian cells when introduced in such cells.

"Replicon" is a molecule that replicates autonomously in host cells. For the purpose of this invention a "replicon" is an RNA sequence "derived" from the corresponding virus (a pestivirus in the case of a pestivirus replicon) comprising all nucleotides required for replication in cells. "Derived" means that the replicon still comprises all nucleotides of the untranslated 5'- and 3'-terminal regions of the genome, as well as of the regions coding for NS3-NS4A-NS4B-NS5A-NS5B of the corresponding virus, but may comprise additional nucleotides that do not interfere with replication.

Preferred are replicons according to the invention derived from classical swine fever virus (CSFV).

The CSFV replicon offers advantages as a carrier of foreign genetic material for human application due to the fact that it is derived from an animal virus which does not infect or otherwise cause harm to humans. As an RNA molecule, it replicates in the cytoplasm of cells, but not in the nucleus. Therefore, it does not present a risk to humans, or other animals, or their cells, as is the case with viral DNA. Moreover, the replicon according to the invention can translate the carried foreign genes into functionally active and complete proteins, but cannot replicate to produce infectious progeny virus, yet another safety component offered by the replicon of the invention. With the translated proteins, the replicon offers the advantage of being able to deliver genes encoding proteins applicable for therapeutic or prophylactic use. In addition, the genes delivered can translate into proteins for processing by the immune system. The replicon can replicate and translate proteins in the dendritic cells of the immune system, critically important for the presentation of such proteins to the immune system leading to the development of immune responses. Thus, the replicon offers high potential as a vaccine, and such vaccines are also an object of the present invention.

As a particular example it is demonstrated herein below that a replicon according to the invention derived from classical swine fever virus carrying the luciferase gene or the influenza virus haemagglutinin gene can be used in an application as a vaccine delivery system. In the particular examples, the foreign genetic material is inserted close to the 5' end of the $N^{pro}$ gene of the replicon, in order to maintain the autoproteolytic activity of $N^{pro}$, i.e. creating a monocistronic replicon. Upon translation of the monocistronic replicon the foreign protein of interest is synthesized as a fusion protein embedded in the $N^{pro}$ polypeptide. Alternatively, the foreign gene is inserted immediately downstream of the $N^{pro}$ gene. In this case, the foreign gene is followed by a stop codon and an IRES (internal ribosome entry site) derived from the EMC (encephalomyocarditis) virus (EMCV) which allows translation of the residual viral polyprotein. Thus, this type of replicon is bicistronic, the first cistron consisting of the $N^{pro}$ gene and the foreign gene of interest and the second cistron carrying the remaining genetic information of the replicon. Upon translation of the bicistronic replicon the autoproteolytic activity of $N^{pro}$ generates the authentic foreign protein of interest.

In particular, the replicon of the invention lacks essential codons or all codons in the gene(s) encoding structural protein(s) required to form infectious virus particles. Such structural proteins are the capsid protein C and the three envelope glycoproteins $E^{rns}$, E1, and E2. It is possible that just one of the four structural proteins, C, $E^{rns}$, E1, and E2 is defective or missing, or that two, three or all four structural proteins are defective and/or missing. An "essential codon" means that if such a codon is lacking then the encoded protein is defective and cannot act as a structural protein, in particular as the structural protein C, $E^{rns}$, E1, or E2.

The replicon of the invention carries a foreign gene. A "foreign gene" is a complete foreign gene or a foreign nucleotide sequence coding for a foreign polypeptide consisting of at least eight amino acids, for example consisting of between 8 and 2000 amino acids, preferably more than 20 amino acids, in particular more than 100 amino acids. "Foreign" designates that the corresponding gene or nucleotide sequence is not found in the pestivirus, but is excised from another source and introduced into the replicon, or is constructed ab initio and introduced into the replicon. Particular examples of foreign genes are genes coding for therapeutic proteins (e.g. hormones such as insulin, cytokines such as GM-CSF, enzymes such as retinal dehydrogenase, cytokine receptors such as TNF receptor) and for proteins present in infectious agents causing diseases, in particular surface proteins of disease-causing viruses (e.g. influenza virus, human immuno-deficiency virus HIV, hepatitis C virus HCV, hepatitis B virus HBV, measles virus, respiratory syncytial virus RSV, and the like), bacteria (e.g. *bordetella* spp, *borelia* spp) or other infectious agents such as parasites (e.g. *Plasmodium* spp) and fungi (e.g. *Candida albicans, Aspergillus fumigatus*), as well as toxins (e.g. tetanus toxoid). Furthermore, nucleotides coding for any of the known immunogenic epitopes of the above mentioned agents may be introduced, for example immunodominant epitopes of the influenza virus HA glycoprotein, the RSV F glycoprotein, or of the HCV E glycoprotein.

The foreign gene may, for example, be inserted at the 5' end of the viral coding sequence, within the first 12 nucleotides at the 5' end of the $N^{pro}$ gene or immediately downstream of the $N^{pro}$ gene. Alternatively, the foreign gene may be introduced in other sites of the virus genome, for example at the beginning of the 3' NTR. Monocistronic and bicistronic replicons with the foreign gene (Gene of Interest, "GoI") inserted as shown in FIG. 2 are preferred. However, the invention is not limited to $\Delta E^{rns}$ or AC-NS2 constructs of FIG. 2. Corresponding monocistronic and bicistronic constructs ΔE1, ΔE2, ΔC and ΔC-E2 (see FIG. 1 C to F) or constructs with partial deletions of structural genes or with other combinations of deletions of structural genes are also envisaged.

The bicistronic replicon offers the advantage that an authentic foreign protein can be synthesized from the replicon due to the ability of $N^{pro}$ to cleave itself at its carboxy terminus to release the downstream protein. The monocistronic replicon from which the foreign sequence is expressed as a fusion protein might be advantageous when short peptides or peptides with poor immunogenicity are considered for expression.

The replicons are constructed to carry an active or inactive form of the $N^{pro}$ gene, in terms of the capacity of the gene product to inhibit the type I interferon induction pathway. In this context, the replicon may lack the $N^{pro}$ gene ($\Delta N^{pro}$ CSFV replicon), or have the $N^{pro}$ gene mutated (indicated as $N^{pro}$ in FIGS. 1 and 2), for example by introducing a cysteine to arginine change at amino acid position 112 of $N^{pro}$ ($C_{112}R$) or an aspartic acid to asparagine change at position 136 ($D_{136}N$). Concerning the latter, each mutation by itself does abolish the capacity of the NPR° gene product to inhibit the type I interferon induction pathway without modifying other functions of the $N^{pro}$ gene product. However, mutation of the $N^{pro}$ gene at both positions further increases the stability of the mutant with respect to the likelihood of reversion, without affecting other functions of the $N^{pro}$ gene product. Depending on the application, replicons with an inactive $N^{pro}$ gene product will have value with respect to inducing type 1 interferon in terms of its function as an antiviral agent and/or immunoregulatory protein. Such applications have value in the context of the replicon functioning, for example, as a vaccine. On the other hand, it may be more desirable that replicons delivering genes encoding therapeutic substances do not induce type 1 interferon. For such replicons, an active $N^{pro}$ is desirable, such that the encoded therapeutic substance can be active without complications ensuing an induction of type 1 interferon.

A particular form of the replicon lacks the sequences coding for C through NS2 ($\Delta$C-N52) and consequently is cytopathogenic. This is advantageous as it has been shown that dying cells are particularly attractive to the immune system for cross-presentation, an important activity with respect to the induction of cytotoxic immune defenses (Racanelli et al., Immunity 20, 47-58, 2004). A cytopathogenic replicon may also be generated in which one or more structural protein genes are present, but the gene encoding NS2 lacks essential or all codons such that the NS2 protein is no longer functional, or the genes encoding NS2 and NS3 are physically separated by additional nucleotides, for example by an IRES.

The replicon designed for expression of any foreign gene of interest retains all genetic information required for its replication in a mammalian cell, in particular in a human cell. Since it replicates in the cytoplasm of the host cell, it avoids the necessity for host cell nuclear division, integration into the host genome or other undesirable effects as are associated with the use of DNA vectors as a vaccine. The replicon causes translation of inserted heterologous genes into proteins for therapeutic or prophylactic use.

The particular replicon described in the "Examples" is based on the plasmid cDNA clone pA187-1 of the CSFV strain Alfort/187. Plasmid pA187-1 contains a T7 promoter immediately upstream of the viral genome sequence and a unique SrfI restriction site at the 3' end of the genome sequence. Thus, linearization of the plasmid DNA with SrfI followed by run-off transcription allows the synthesis of authentic viral RNA. As shown by Ruggli et al. (J Virol 70, 3478-87, 1996) this RNA is infectious when tested in swine kidney cells lines, including SK-6 cells, giving rise to the synthesis of infectious progeny virus after transfection of the cells. However, this known RNA does not carry a foreign gene, but is only encoding genes of the CSFV strain Alfort/187.

In the present invention, a foreign gene is introduced into the replicon. The replicon RNA is tested for replicative or translation potential in cells of the immune system, particularly dendritic cells, in view of the envisaged application, i.e. promoting an immune response. A replicon according to the invention carrying a luciferase gene as the foreign gene does in fact translate functional luciferase protein following transfection into porcine dendritic cells.

The particular replicons of the invention tested lack the sequence coding for either one of the four viral structural proteins C, $E^{rns}$, E1 or E2, or they lack the coding sequence for all four viral structural proteins C, $E^{rns}$, E1 and E2. Cytopathogenic replicons lack in addition the genes encoding the nonstructural proteins p7 and NS2. All replicons are obtained by the same means as the known infectious RNA obtained from pA187-1. No limitations to the size of the replicon are expected. These replicons replicate after transfection into eukaryotic cells, but due to the lack of structural proteins no infectious virus is generated. Packaging of the replicons is still possible in cell lines stably transduced to express the respective protein(s).

Figure 2:
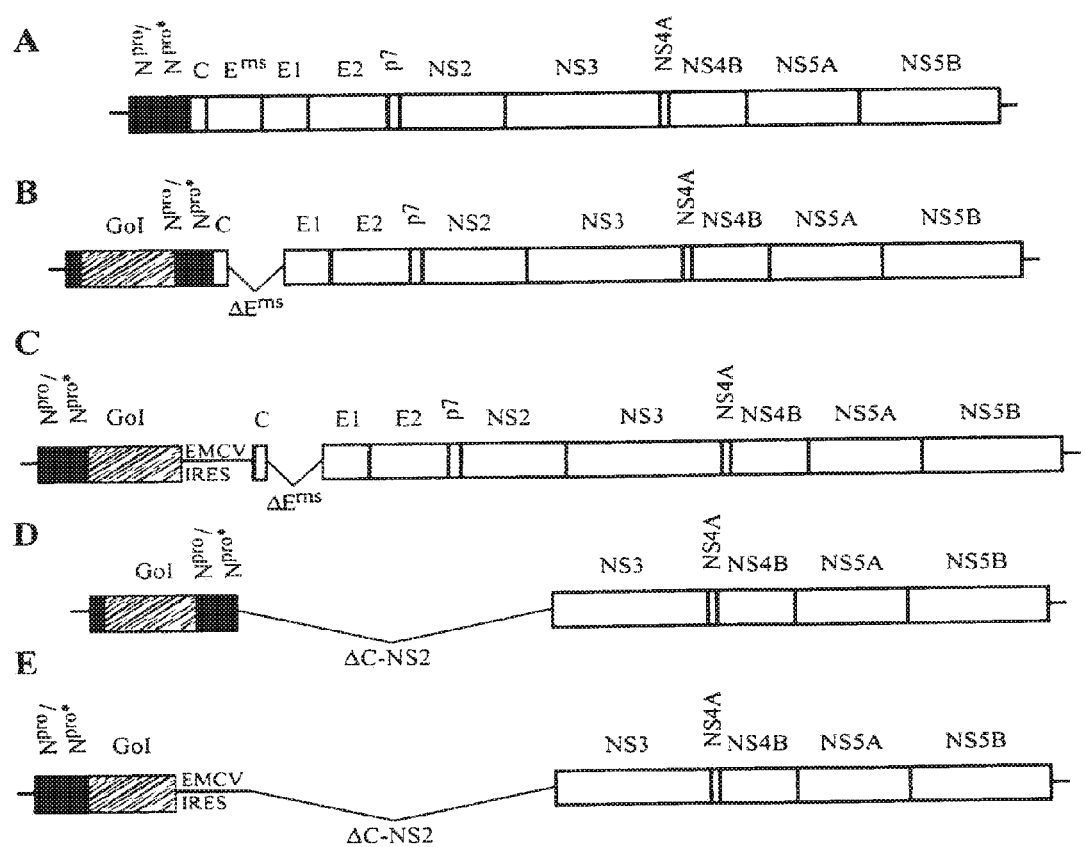

FIG. 1 shows examples of the deletions which can be employed for the construction of the replicons. FIG. 2 shows examples of how a gene of interest (GoI) can be inserted into the replicon genome. In this case, the figure shows examples of the two forms of replicon designed for expression of a foreign protein, either monocistronic or bicistronic. For each of the two forms, the figure also shows an example of the deletions in the structural gene region, exemplified with the deletion of a single gene, the $E^{rns}$ gene. An example is also shown in which multiple gene deletion is employed—deletion of the genes C to NS2 inclusive. Any replicon which still encodes an active NS2 is non-cytopathogenic. In order to generate cytopathogenic replicons, additional deletion of NS2 is required, as depicted in FIG. 1G and FIGS. 2 D, E.

FIGS. 1 and 2 also represent the two forms of the $NP^{pro}$ gene: The intact $N^{pro}$ gene, whose product impairs the capacity of the cell to be induced for type I IFN production, or the mutated $N^{pro}$ gene ($N^{pro}$), whose product cannot prevent type I IFN induction. The use of a construct without a $N^{pro}$ gene has the same consequence as the use of construct with a mutated $N^{pro}$ gene in terms of influencing the cell inducibility for type I IFN production.

The positioning of the GoI insert must not interfere with the replication and translation of the replicon genes themselves. The preferred positions for this foreign gene is insertion close to the 5' end of the viral coding sequence, within the $N^{pro}$ gene or at the 3' end of the $N^{pro}$ gene. These insertion positions are selected to avoid any risk that the inserted foreign gene is not tolerated within the replicon construct. The presence of the foreign gene in these positions does not interfere with the replication and translation of the replicon.

In the particular example described below, the monocistronic or bicistronic replicon constructs carry a unique NotI site for insertion of the foreign gene sequence, such as the luciferase gene or the influenza virus HA gene. In the case of the monocistronic replicon, the insertion occurs within the N-terminal part of $N^{pro}$. By this means a fusion protein is generated composed of the 11 N-terminal amino acid residues of $N^{pro}$, followed by the residues Thr-Asn-Lys, the foreign protein, the residues Thr-Asn-Lys and the remaining C-terminal part of $N^{pro}$ (amino acid residues 15 to 168). Insertion at this position does not affect either of the two functions of $N^{pro}$, namely autoproteolytic activity responsible for cleavage of $N^{pro}$ from the nascent polyprotein, and interference with the innate immune response in terms of interference with the induction of type I IFN in the cell.

In the particular example of the bicistronic replicon described below, the foreign gene is inserted immediately after the N$^{pro}$ gene, and is followed by a stop codon and an internal ribosome entry site (IRES) derived from the picornavirus encephalomyocarditis virus (EMCV), for translation initiation of the remaining viral polyprotein (C to NS5B or NS3 to NS5B). The important feature of this vector is that authentic foreign protein can be expressed whereas in the monocistronic replicon it is synthesized as a fusion protein with the N$^{pro}$ protein.

The particular monocistronic and bicistronic constructs involving the N$^{pro}$ gene have been generated without compromising the translation and replication of the replicon. The replicon can be genetically manipulated at this site without deference to the functionality of the replicon.

The foreign gene insert must remain functional and be stably expressed by the replicon. Moreover, the insert must not interfere with the correct operation of the pestivirus replicon genes, particularly in terms of their replication and the translation of their encoded genes. The present invention provides solutions demonstrating (i) the tolerance of the foreign gene insert in the replicon, (ii) the retention of functionality by the foreign gene in terms of its correct translation into the encoded protein, (iii) the retention of functionality by the replicon following insertion of large pieces of genetic information as contained within the foreign gene insert.

Pestivirus replicons have high potential as vaccines. Due to the fact that they are non-infectious (do not give rise to infectious virus) and hence non-transmissible, they also fulfill a major criterion for a safe vaccine.

The present invention relates also to pharmaceutical compositions that comprise a pestivirus replicon as defined herein before as the active ingredient, optionally with further pharmaceutically acceptable components. Compositions for enteral administration, such as nasal, buccal, rectal or, especially, oral administration, and for (the particularly preferred) parenteral administration, such as intravenous, intramuscular or subcutaneous administration, to warm-blooded animals, especially humans, are preferred.

For the application of the replicon in pharmaceutical preparations, including vaccines, the replicon may be used as naked RNA. This requires protection of the RNA against RNase degradation, such as by RNA capping. Alternatively, the pestivirus replicon may be associated with appropriate particulate delivery vehicles. These may enhance protection of the RNA, while also increasing the efficiency for delivery of the RNA to the cells in which the RNA will translate its encoded proteins. To this end, the RNA is encapsulated into the particulate delivery vehicle during the production of the latter, or is added to the pre-formed particles. In either case, the complimentary charges of the RNA and the particles can be used to enhance the interaction of the RNA with the particles. Alternatively, the RNA can be physically linked to the particles via a linker such as polyethylene glycol modified particle surfaces. Examples of such particulate vehicles with potential for RNA delivery are liposomes, microparticles, nanoparticles or nanocapsules. Liposomes, microparticles, nanoparticles or nanocapsules as drug carriers are well known in the art, and these are considered here as particulate delivery vehicles.

The aforementioned particulate delivery vehicles may be modified to incorporate structural proteins of the pestivirus. In this sense, another particulate delivery vehicle considered is the virus replicon particle (VRP) comprising the replicon of the invention. The virus replicon particle consists of structural proteins of a pestivirus. Such virus replicon particles may be obtained by culturing replicons of the invention in cell lines expressing those structural proteins that are not encoded in proper form by the replicon of the invention. The virus replicon particle obtained may then be used in pharmaceutical preparations and applied to mammalians. The properties of the replicon of the invention being part of the virus replicon particle makes sure that virus replicon particle is not infective, but replicates and expresses the foreign gene at the delivery point of the virus replicon particle. However, VRP based on the CSFV particle without further modification are unlikely to be efficient delivery vehicles for targeting human cells, because the CSFV itself does not infect human cells. Such a VRP is modified to carry a protein or protein sequence enhancing the targeting of human cells. Examples considered are the inclusion of tetralysine peptides for targeting heparan sulphate structures, as well as mannosylation or addition of N-acetyl-glucosamine derivatives for enhanced targeting of C-type lectin receptors.

Cell lines considered for the preparation of pestivirus replicon particles of the invention are porcine or human cells lines stably transduced to provide the structural proteins not encoded or only encoded in defective form by the replicon of the invention. Such virus replicon particles are safe in that they are not able to replicate into infectious virus particles.

The pharmaceutical compositions comprise the pestivirus replicon alone or associated with appropriate particulate delivery vehicles and, preferably, together with a pharmaceutically acceptable carrier. The dosage of the pestivirus replicon depends upon the disease to be treated and upon the species, its age, weight, and individual condition, the individual pharmacokinetic data, and the mode of administration.

For parenteral administration, preference is given to solutions of the pestivirus replicon, and also suspensions or dispersions, especially isotonic aqueous solutions, dispersions or suspensions which, for example in the case of lyophilized compositions comprising the pestivirus replicon alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinyl-pyrrolidone, or gelatins, or also solubilizers, e. g. Tween 80 (polyoxyethylene (20) sorbitan mono-oleate). Preferred preservatives are, for example, antioxidants, such as ascorbic acid, or microbicides, such as sorbic acid or benzoic acid.

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers. Solutions such as are used, for example, for parenteral administration can also be employed as infusion solutions.

Particular pharmaceutical compositions considered are vaccines, wherein the replicon of the invention encodes proteins present in infectious particles causing diseases, in particular surface proteins of disease-causing viruses, bacteria or other infectious agents, or other known immunogenic epitopes. Such vaccines may contain adjuvants customarily used in vaccines, antimicrobial peptides, and also immunostimutatory nucleic acids that are able to facilitate and/or improve adaptive immune responses. Examples are GM-CSF encoded by the replicon, or formulation of the replicon in or with known immunomodulatory entities such as oil-based adjuvants, CpG-oligodeoxynucieotides, lipopeptides, immunomodulatory peptides, and the like.

Furthermore the invention concerns a method of prophylaxis against a disease caused by an infectious agent, comprising administering a pestivirus replicon of the invention, wherein the foreign gene encodes a gene product immunizing against the infectious agent. Particular diseases considered are, for example, diseases caused by influenza virus, HIV, HCV, HBV, measles virus, RSV, bordetella spp, borelia spp, Plasmodium spp, Candida albicans, Aspergillus fumigatus, tetanus toxoid, and the like. In the method of the invention the pestivirus replicon to be administered comprises a suitable epitope or gene product from the mentioned infectious agents.

Furthermore, the invention concerns a method of treatment of a disease caused by a deficient gene, by administering a replicon, alone or associated with appropriate particulate delivery vehicles, wherein the foreign gene incorporated into the replicon is the functional gene associated with the disease. Examples are FGF4, an angiogenic protein that enhances the formation of new blood vessels for treatment of coronary artery disease; potassium channel genes for inner ear therapy; gene therapy for patients with XSCID, ADA-deficient SCID and chronic granulomatous disease; alpha1 Me/alpha1ATp for promoting hepatic HMB-synthase expression; angiopoietin-1 gene therapy for modulating the pulmonary vascular response to lung injury.

EXAMPLES

Example 1

Construction of the CSFV Replicons

The CSFV replicon can replicate in target cells, but is incapable of producing infectious virus unless assisted by propagation in specialized "packaging" cell lines in vitro. This is characterized in that the replicon expresses all structural proteins of a pestiviruses except for E1 protein, or E2 protein, or $E^{rns}$ protein, or C protein, or combinations or parts thereof.

Plasmid Constructs

Mutant CSFV genomes are constructed on the basis of the full-length cDNA clones pA187-1. Plasmids are amplified in E. coli XL-1Blue cells (Stratagene), and plasmid DNA purified with Nucleobond DNA purification system (Macherey Nagel). These constructs are based on the published sequences of the full-length cDNA clone pA187-1 (Ruggli et al., J Virol 70, 3478-3487, 1996). The plasmids containing the full-length viral cDNA are linearized with SrfI (Stratagene) and purified by phenol-chloroform extraction and ethanol precipitation. The pellet is resuspended in RNase-free $H_2O$ to a final concentration of 500 ng/ml. In vitro transcription is performed by using a MEGAscript T7 kit (Ambion). As instructed by the supplier, a 20 µl reaction mixture containing 1.5 µg of linearized plasmid DNA, 13 µl transcription buffer, 7.5 mM each ATP, CTP, GTP, and UTP and 2 µl of T7 polymerase-RNase inhibitor mix is incubated at 37° C. For removal of template DNA, the reaction mixture is subsequently incubated for 15 min at 37° C. in presence of 2 units DNase I. RNA from transcription reactions is purified by phenol-chloroform extraction and precipitation in the presence of 500 mM ammonium acetate, 10 mM EDTA, and 1 volume of isopropanol. Alternatively, after DNase I digestion, transcripts are purified through MicroSpin S-400 HR columns (Pharmacia) and quantified with a GeneQuant II photometer (Pharmacia).

Replicon Constructs

Viral cDNA lacking the $E^{rns}$ gene (alternatively lacking E1, or E2, or C, or any combination of these) is used as replicon (FIG. 1). For the monocistronic constructs, the foreign gene (for example influenza virus HA gene) is inserted into a unique NotI site introduced into the amino-terminal region of the $N^{pro}$ gene. The obtained fusion protein has 739 amino acids (aa) and is composed of $N^{pro}$ (aa 1-11)-Ser-Gly-Arg-HA (aa 1-568)-Gly-Gly-Arg-$N^{pro}$ (aa 15-168). Known activities of $N^{pro}$—such as the autoprotease activities, interference with type I IFN-induction pathway, and degradation of interferon regulatory factor 3 (IRF3)— are maintained. A variation of the construct is obtained by introducing mutations for $C_{112}R$ or $D_{136}N$ into the $N^{pro}$ sequence, to generate a replicon that does not regulate type I IFN induction or production.

Bicistronic viral cDNA lacking the $E^{rns}$ gene is also used as replicon (deletion of E2 or C is also possible. The first cistron contains the $N^{pro}$ gene fused in frame to the foreign gene (influenza virus HA gene SEQ ID NO: 13) followed by the EMCV IRES that initiates translation of the remaining viral polyprotein (C to NS5B). From this replicon both $N^{pro}$ (SEQ ID NO: 1) and the influenza virus HA gene are expressed in their authentic form. The activities of $N^{pro}$, autoprotease and regulation of type I IFN induction or production, are maintained. A variation of the construct is obtained by introducing mutations for C112R or D136N into the Npro sequence, to generate a replicon that does not regulate type I IFN induction or production (SEQ ID NOS: 2 and 3, respectively). Alternatively, $N^{pro}$ can be truncated C-terminally by deleting most of the coding sequence. This again generates a replicon that has lost the capacity to regulate type I INF induction or production. The remaining N terminal $N^{pro}$ sequence is then expressed as a fusion to the foreign gene product influenza virus HA protein.

Example 2

Cytopathogenic and Non-cytopathogenic RNA Replicons of Classical Swine Fever Virus Plasmid Constructs The mutant CSFV genomes exemplified by that shown in FIG. 1G are constructed on the basis of the full-length cDNA clone pA187-1 (Ruggli et al., J Virol 70, 3478-3487, 1996). Plasmid DNA constructs are amplified in E. coli XL-1 Blue cells (Stratagene). Restriction enzymes are from New England Biolabs except for SrfI (Stratagene). Plasmid DNA is purified with the Wizard Mini- or Maxiprep kit (Promega). Primers used for reverse transcription (RT) and PCR are as published (Ruggli et al., J Virol 70, 3478-3487, 1996). The derivation of these mutant CSFV genomes is as published (Moser et al., J Virol 73, 7787-7794, 1999).

In vitro Transcription and Electroporation

In vitro transcription from SrfI 12298- or NruI 11301-linearized plasmids is performed by using the T7 Megascript kit (Ambion). After DNase I digestion, transcripts are purified through MicroSpin S-400 HR columns (Pharmacia) and quantified with a GeneQuant II photometer (Pharmacia). SK-6 cells are washed twice and resuspended in ice cold phosphate buffered saline (PBS). A total of 2×107 cells in a volume of 0.8 ml are mixed with 15 µg of RNA, transferred to a 0.4 cm cuvette (Bio-Rad), and electroporated immediately by using a Gene Pulser (Bio-Rad) set at 450 V and 500 F. Alternatively, 0.4 ml of cell suspension at a density of 107 cells/ml is mixed with 5 mg of RNA, transferred into a 0.2 cm cuvette, and electroporated twice at 200 V and 500 µF. After electroporation the cell suspension is kept for 10 min at room temperature, then diluted in Dulbecco's modified Eagle medium containing 5% (v/v) horse serum, seeded, and harvested for analysis at different times after electroporation.

RNA Analysis

Total RNA is extracted from 5×10$^6$ electroporated cells with Trizol reagent (Gibco). Irrespective of the RNA concentration, one third of each sample is used for Northern blotting to standardize the samples based on the number of electroporated cells. Northern blotting and hybridization are performed with $^{32}$P-labelled riboprobes: either JL1, which is complementary to the 3'-terminal 204 nucleotides (nt), for the detection of positive-stranded viral RNA of the CSFV Alfort/187 genome, or GM, corresponding to nt 327 to 582 of the CSFV Alfort/187 genome for the detection of negative-stranded RNA. RT reactions are performed by using the Expand RT kit (Boehringer Mannheim), primer HR3, and MicroSpin S-400 HR columns for subsequent cDNA purification. For PCR either the Expand long-template PCR kit (Boehringer Mannheim) or, for amplification of fragments shorter than 1 kb, Taq DNA polymerase (Promega) is used.

Protein Analysis

SK-6 cells are lysed in a hypotonic buffer (20 mM MOPS (morpholinopropanesulfonic acid], 10 mM NaCl, 1.5 mM MgCl2, 1% Triton X-100 [pH 6.5]), and the extracts used for Western blotting. Porcine anti-pestivirus hyperimmune serum N8T12 and MAb 49DE directed against pestivirus NS3 protein served for the detection of the NS3 protein.

Packaging of Replicon RNA

After electroporation of defective genomes together with full-length helper A187-CAT RNA, 5×10$^6$ SK-6 cells are incubated for 48 h before the virus is harvested by freezing and thawing of the cultures. After low-speed centrifugation, 1 ml of undiluted supernatant is used to infect 2×10$^6$ SK-6 cells seeded the day before, and the inoculum replaced after 1 h. An aliquot of the cell culture medium is collected 48 h after infection for RNA extraction and RT-PCR.

Example 3

Construction of CSFV Deletion Mutants

E2 Deletion Mutants

E2 deletion mutants, such as pA187-E2del373 and pA187-E2del168, are constructed as follows (Maurer et al., Vaccine 23, 3318-3328, 2005). Their schematic representations are shown in FIG. 10. Deletion of either the complete E2 gene (nucleotides 2441-3559 of the CSFV vA187-1 genome) encoding 373 amino acids or of nucleotides 3248-3451 encoding 68 amino acids of E2 is obtained by PCR-based site-directed mutagenesis using the cDNA plasmid clone pA187-1 as template. The nucleotide numbers refer to the genome of vA187-1 (GeneBank accession number X87939). Two complementary oligonucleotide primers with an overlap of 20 nucleotides at their 5' ends and representing the 5' and the 3' sequence with respect to the required deletion are used. Each of the two mutagenesis primers are used together with a forward or reverse primer representing a sequence located upstream or downstream of the deletion, respectively, to generate one PCR fragment each. The reactions are performed with Pfu Turbo Polymerase for 20-30 cycles of amplification. For assembly, the two PCR fragments are isolated by agarose gel electrophoresis and submitted to additional 30 cycles of PCR using the respective primers flanking the expected fusion product. Subsequently, Taq polymerase (Promega) is added for 15 min at 72° C. to obtain 5'-terminal adenosylation of the PCR product before purification from an agarose gel and insertion into plasmid pCR-XL-TOPO (Invitrogen). The respective inserts are sequenced with the Thermo Sequenase™ DYEnamic direct cycle sequencing kit (Amersham Biosciences) and analysed on a LI-COR 4200 sequencer using e-Seq and AlignlR software (LI-COR Biosciences). The required restriction fragments are isolated from the pCR-XL-TOPO subclones and used to replace the corresponding sequences in the full-length cDNA clone pA187-1 to obtain the E2 deletion mutants. The specific infectivity of the RNA, expressed as infectious units (IU) per microgram of RNA, is determined in the infectious centre assay employed for in vitro synthesized CSFV RNA (see below).

E$^{rns}$ Deletion Mutants

Deletion of the complete Ems gene (nucleotides 1175 to 1855 of the CSFV vA187-1 genome) encoding 227 amino acids is obtained by PCR-based site directed mutagenesis (Frey et al., Vet Res 37, 655-70, 2006). The schematic representation is shown in FIG. 1 B. A PCR fragment containing the Ems deletion is used to replace the corresponding region in the full-length cDNA clone pA187-1 to obtain the mutant pA187delEm5. Run-off in vitro transcription of SrfI linearized pA187delEms is performed.

Characterization of the Deletion Mutant RNAs

The in vitro synthesized RNA (10 µg) is electroporated into SK-6 cells. One tenth of the electroporated cells are seeded into two wells of a 24-well plate for staining by immunoperoxidase or immunofluorescence assay using either anti-NS3 mAb C16 or anti E2 mAb HC/TC26. The specific infectivity of the RNA, employed for in vitro synthesized CSFV RNA and expressed as infectious units (IU) per microgram of RNA, is determined in the infectious centre assay. Thus, one tenth of the electroporated cells are diluted in 2 ml EMEM-HS and seeded in six-well plates, and serially diluted. After incubation at 37° C. for 3 days, the cells are fixed and positive cells visualized by immunoperoxidase or immunofluorescence assay using either anti-NS3 mAb C16 or anti-E2 mAb HC/TC26.

Characterization of CSFV-VRP Deletion Mutants

In addition to constructing the replicons themselves, it is also possible to produce virus replicon particles (VRP) as required. The mutant RNAs are electroporated into a "complementing cell line" of SK-6 cells stably expressing the viral E2 or Ems protein, to generate mutant RNAs packaged into virus-like particles, termed CSFV virus replicon particles CSFV-VRP. In order to verify that CSFV replicons are stable in complementing cells the respective region of the CSFV-VRP genome (=the replicon) is amplified by RT-PCR and sequenced. To this end, cytoplasmic RNA is obtained by Trizol extraction (Invitrogen) of SK-6 cell cultures infected with the VRP. RT-PCR is performed with Expand reverse transcriptase (Boehringer) and Taq polymerase (Promega). The primers used for the E2 deletion mutants are ZR4 (nucleotides 4178-4148 of the CSFV genome) for cDNA synthesis and ML5 (nucleotides 2196-2213)/ZR5 (nucleotides 3892-3862) for PCR. These primers map in the flanking regions of the E2 gene and are not expected to anneal to E2 contained in SK-6 (complementary) cells. The primers used for the E$^{rns}$ deletion mutants are PR1 (nucleotides 6454-6434 of the CSFV Alf/187 genome) for cDNA synthesis and ML1 (nucleotides 992-1022)/MR3 (nucleotides 1956-1940) for PCR. The latter two primers map in the flanking regions of the E$^{rns}$ gene on the viral genome and therefore are not expected to anneal to Ems DNA contained in the SK-6 (complementary) cells. The amplified DNA fragments are characterized by agarose gel electrophoresis.

Example 4

Confirmation that CSFV Leader Proteinase NPro is not Required for Replicon Replication In order to ascertain that N$^{pro}$ is not essential for the viability of the replicon, and therefore the virus, a mutant CSFV genome vA187-Ubi is constructed, in which the N$^{pro}$ gene is replaced by the murine ubiquitin gene released from plasmid pTM3/HCV/Ubi-NS5B (Tratschin et al., J. Virol 72, 7681-84, 1998). For generation of infectious vA187-Ubi virus, pA187-Ubi DNA is linearised with SrfI, followed by in vitro RNA transcription, and lipofection of the RNA into porcine SK-6 cells. 48 hours after transfection, the cells are tested for expression of viral envelope protein E2 by the immunoperoxidase assay. Analysis of the viral RNA is by reverse transcription (RT)-PCR.

Two additional mutants have been generated: CSFV vA187-ΔN$^{pro}$ in which the N$^{pro}$ gene is replaced by the residues methionine and glycine; CSFV vEy-ΔN$^{pro}$ in analogy to vA187-ΔN$^{pro}$ by deleting the ΔN$^{pro}$ gene in the pEy-37 cDNA clone (Ruggli et al., J. Virol 77, 7645-54, 2003). Replacement of the N$^{pro}$) in any of these viruses does not prevent the virus from replicating. The vA187-Ubi virus, also termed vA187-ΔNP$^{pro}$-Ubi or ΔN$^{pro}$-Ubi virus, replicates to titres similar to those of the parent vA187-1 virus, when the non-interferon producing SK-6 cells are employed. The ΔN$^{pro}$ viruses also replicate in the interferon-producing PK-15 cells and porcine macrophages. In these cells, there is a longer lag phase in the replicative cycle, and titres which are lower by 1.5 to 2 $\log_{10}$ TCID$_{50}$/ml are obtained compared with the parent virus. Nevertheless, the ΔN$^{pro}$ viruses are clearly replication competent. The lower titres are due to the inability to control induction of type I interferon (see below under Example 5).

Example 5

Characterization of Replicons With and Without the CSFV Leader Proteinase N$^{pro}$ With Respect to the N$^{pro}$-dependent Interference With Cellular Antiviral Defense The vA187-Ubi virus, also termed ΔN$^{pro}$-Ubi virus, together with vA187-ΔN$^{pro}$ and vEy-ΔN$^{pro}$ (see Example 4) have been used to demonstrate the role of NPR° in cellular anti-viral defence control (Ruggli et al., J. Virol 77, 7645-54, 2003). Macrophages are mock infected or infected with either standard CSFV or the mutant virus, followed by stimulation of the cells with the interferon (IFN) inducer poly(IC). The cells can also be electroporated with the viral genomes or replicon RNA. Supernatants from the infected cell cultures are tested for antiviral activity either in the VSV plaque reduction assay or in the Mx/CAT reporter gene assay. The same results were obtained in both assays.

Figure 3:
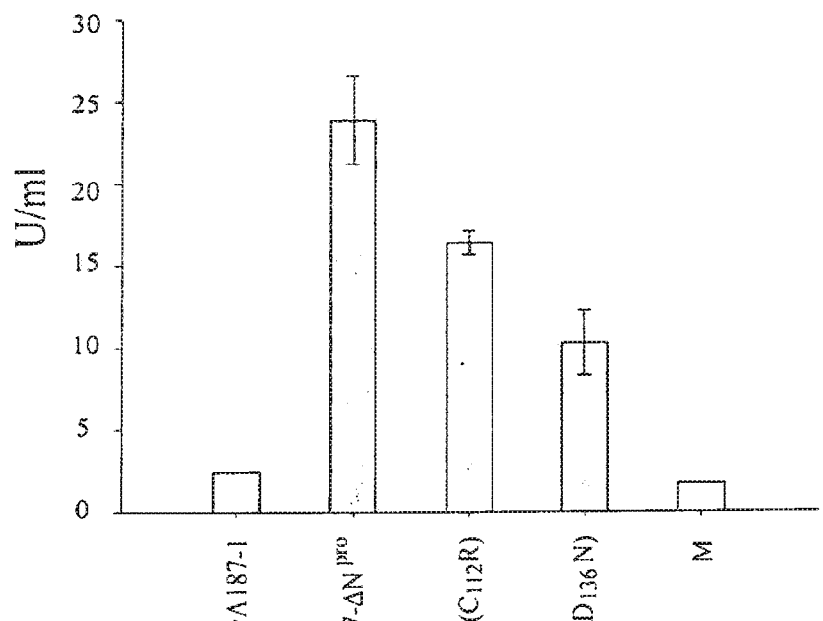
Figure 3:
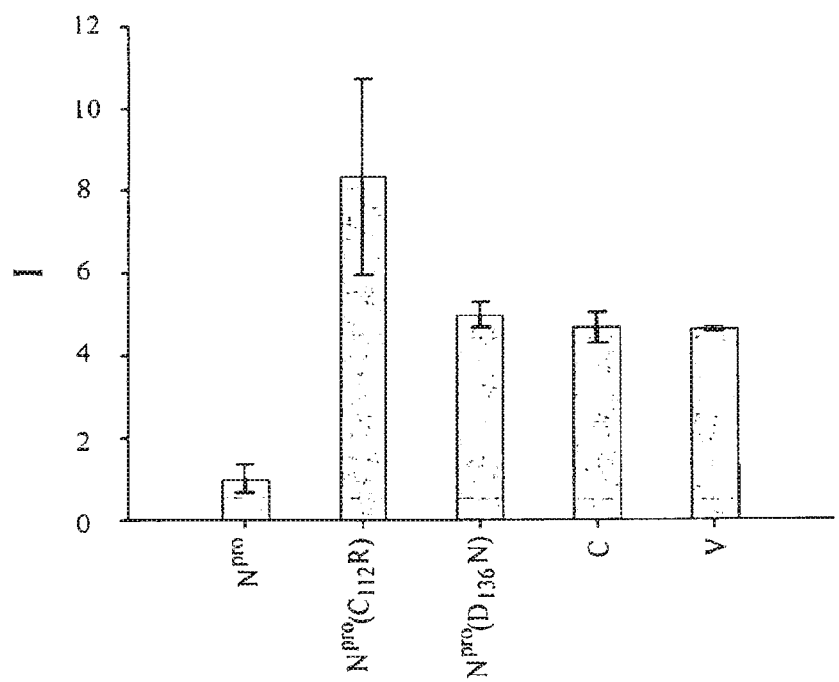

Standard CSFV does not induce antiviral activity or type I IFN production (FIG. 3A; vA187-1). When the viral N$^{pro}$ gene is deleted (vA187-ΔN$^{pro}$), or when the N$^{pro}$ gene is mutated at positions 112 (vA187-N$^{pro}$(C$_{112}$R)) or 136 (vA187-N$^{pro}$(D$_{136}$N)), the virus now induces type 1 IFN production (FIG. 3A). This observation is due to the ability of the N$^{pro}$ protein to control the cellular pathway leading to the induction of Type 1 IFN (Ruggli et al., J. Virol 77, 7645-54, 2003). This has been confirmed using transfection of plasmids encoding an intact N$^{pro}$ protein or a mutated form, carrying a cysteine to arginine substitution at amino acid position 112 of N$^{pro}$ (N$^{pro}$(C$_{112}$R)) or an aspartic acid to asparagine substitution at position 136 (N$^{pro}$(D$_{136}$N)). When macrophages are stimulated with poly(IC), up to 40 U of type 1 IFN/ml can be detected. The presence of a CSFV-infection in the macrophages can abrogate this poly (IC) induction of IFN, whereas ΔN$^{pro}$ and mutated N$^{pro}$ viruses cannot prevent the poly(IC) induction of type 1 IFN. Similarly, when cells, including the human HEK293T cells, are transfected with a construct encoding the N$^{pro}$ protein, there is an inhibition of poly(IC)-induction of type 1 IFN (FIG. 3B). When the cells are transfected with a construct encoding for the mutant forms of the N$^{pro}$ protein (N$^{pro}$ (C112R); (N$^{pro}$(D$_{136}$N)), the cells regain their capacity to respond to poly (IC) with type 1 IFN production (FIG. 3B).

The invention is claimed as follows:

1. A method of prophylaxis against a disease caused by an infectious agent, the method comprising administering to a mammal a composition comprising a particulate delivery vehicle comprising a single-stranded RNA pestivirus replicon lacking essential codons or all codons for one or more structural proteins required for formation of infectious virus, and carrying a foreign gene encoding a gene product immunizing against the infectious agent or the disease-causing moiety, wherein the single-stranded RNA pestivirus replicon is encapsulated inside the particulate delivery vehicle to protect the single-stranded RNA pestivirus replicon against RNase degradation and wherein the particulate delivery vehicle is appropriate to deliver the single-stranded RNA pestivirus replicon to the cytoplasm of cells for replication and translation of the single-stranded RNA pestivirus replicon in the cytoplasm.

2. The method of claim 1, wherein the composition is administered by oral, nasal and/or buccal administration.

3. The method of claim 1, wherein the particulate delivery vehicle is selected from the group consisting of liposomes, microparticles, nanoparticles and nanocapsules.

4. The method of claim 1, wherein the particulate delivery vehicle is a Virus Replicon Particle (VRP).

5. The method of claim 1, wherein the pestivirus replicon is a classical swine fever virus (CSFV) replicon, which is noncytopathogenic and comprises a p7 gene.

6. The method of claim 1, which comprises the step of inducing, in the mammal to which the composition is administered, an adaptive, humoral immune reaction against the infectious agent.

7. The method of claim 1, wherein the mammal is a human subject.

8. The method of claim 1, wherein the mammal is a pig.

9. The method of claim 1, wherein an N$^{PRO}$ gene of the replicon is mutated or C-terminally truncated, wherein the replicon cannot prevent type I IFN induction, and wherein an autoproteolytic activity of the N$^{PRO}$ gene is maintained.

10. The method of claim 9, wherein the $N^{PRO}$ gene is mutated and comprises one or both mutations selected from a mutation at amino acid position 112 (C112R) and a mutation at amino acid position 136 (D136N).

11. The method of claim 1, wherein the replicon comprises an $N^{PRO}$ gene, and wherein the foreign gene is inserted immediately downstream of the $N^{PRO}$ gene, wherein the foreign gene is followed by a stop codon and an internal ribosome entry site (IRES).

12. The method of claim 1, wherein the replicon comprises an $N^{PRO}$ gene encoding an $N^{PRO}$ protein with maintained autoproteolytic activity, and wherein the foreign gene is inserted within the N-terminal part of the $N^{PRO}$ gene.

13. A pharmaceutical composition comprising a particulate delivery vehicle comprising a single-stranded RNA pestivirus replicon lacking essential codons or all codons for one or more structural proteins required for formation of infectious virus, and carrying a foreign gene encoding a gene product immunizing against the infectious agent or the disease-causing moiety, wherein the single-stranded RNA pestivirus replicon is encapsulated inside the particulate delivery vehicle to protect the single-stranded RNA pestivirus replicon against RNase degradation and wherein the particulate delivery vehicle is appropriate to deliver the single-stranded RNA pestivirus replicon to the cytoplasm of cells for replication and translation of the single-stranded RNA pestivirus replicon in the cytoplasm.

14. The pharmaceutical composition of claim 13, wherein the composition is adapted to oral, nasal and/or buccal administration.

15. The pharmaceutical composition of claim 13, wherein the particulate delivery vehicle is selected from the group consisting of: liposomes, microparticles, nanoparticles and nanocapsules.

16. The pharmaceutical composition of claim 13, wherein the particulate delivery vehicle is a Virus Replicon Particle (VRP).

17. The pharmaceutical composition of claim 13, wherein the pestivirus replicon is a classical swine fever virus (CSFV) replicon, which is noncytopathogenic and comprises a p7 gene.

18. The pharmaceutical composition of claim 13, wherein the mammal is a human subject.

19. The pharmaceutical composition of claim 13, wherein the mammal is a pig.

* * * * *